(12) United States Patent
Shergold (10) Patent No.: US 8,568,349 B2
(45) Date of Patent: Oct. 29, 2013

(54) FLOW CONTROL VALVES FOR LEAKAGE DETECTION, FREE-FLOW PREVENTION AND OCCLUSION DETECTION

(75) Inventor: Oliver Shergold, Kirchberg (CH)

(73) Assignee: Roche Diagnostics International AG, Rotkreuz (CH)

( * ) Notice: Subject to any disclaimer, the term of this patent is extended or adjusted under 35 U.S.C. 154(b) by 175 days.

(21) Appl. No.: 13/035,505

(22) Filed: Feb. 25, 2011

(65) Prior Publication Data

US 2012/0059313 A1 Mar. 8, 2012

Related U.S. Application Data

(63) Continuation of application No. PCT/EP2009/060864, filed on Aug. 24, 2009.

(30) Foreign Application Priority Data

Aug. 27, 2008 (EP) ..................................... 08163053

(51) Int. Cl.
*A61M 5/168* (2006.01)

(52) U.S. Cl.
USPC ............................................. 604/67; 604/65

(58) Field of Classification Search
CPC ...................................................... A61M 5/168
USPC ............ 73/204.21; 604/65, 67, 151, 246, 272
See application file for complete search history.

(56) References Cited

U.S. PATENT DOCUMENTS

| | | | | |
|---|---|---|---|---|
| 5,055,001 A | * | 10/1991 | Natwick et al. ................. | 417/63 |
| 5,096,385 A | * | 3/1992 | Georgi et al. .................... | 417/18 |
| 5,219,279 A | * | 6/1993 | Natwick et al. ............... | 417/479 |
| 5,356,375 A | * | 10/1994 | Higley ............................ | 604/30 |
| 6,280,408 B1 | * | 8/2001 | Sipin ............................... | 604/65 |
| 6,368,314 B1 | | 4/2002 | Kipfer et al. | |
| 6,558,347 B1 | * | 5/2003 | Jhuboo et al. ................... | 604/67 |
| 7,366,569 B2 | * | 4/2008 | Belalcazar ....................... | 607/23 |
| 7,566,326 B2 | * | 7/2009 | Duchon et al. ................ | 604/228 |
| 2004/0153029 A1 | * | 8/2004 | Blischak et al. ................ | 604/65 |
| 2005/0234407 A1 | * | 10/2005 | Spohn et al. ................... | 604/253 |
| 2005/0241387 A1 | * | 11/2005 | Miesel et al. ............... | 73/204.21 |
| 2007/0112299 A1 | * | 5/2007 | Smit et al. ........................ | 604/67 |

(Continued)

FOREIGN PATENT DOCUMENTS

| | | |
|---|---|---|
| EP | 0 319 275 A1 | 6/1989 |
| EP | 0 446 897 A2 | 9/1991 |
| EP | 1 247 538 A2 | 10/2002 |

OTHER PUBLICATIONS

International Search Report and Written Opinion dated Sep. 21, 2009 pertaining to International application No. PCT/EP2009/060864 filed Aug. 24, 2009.

*Primary Examiner* — Theodore J Stigell
*Assistant Examiner* — Gerald Landry, II
(74) *Attorney, Agent, or Firm* — Dinsmore & Shohl LLP (57) ABSTRACT

An injection device for injecting a fluid into an organism, in particular a human or animal body, which can comprise a fluid providing section including a container for storing the fluid and a supply means for supplying the fluid. The fluid injecting section for injecting the fluid provided by the fluid providing section into the organism includes a catheter means and is characterized by the fluid injecting section being provided with a pressure recognition arrangement which can be located close to and/or in the catheter means for detecting a pressure increase and/or a pressure loss.

11 Claims, 5 Drawing Sheets

(56) References Cited

U.S. PATENT DOCUMENTS

| | | |
|---|---|---|
| 2007/0112303 A1 | 5/2007 | Liniger |
| 2008/0086087 A1* | 4/2008 | Spohn et al. .................. 604/151 |
| 2009/0171333 A1* | 7/2009 | Hon ................................ 606/21 |
| 2009/0171379 A1* | 7/2009 | Coe et al. ...................... 606/157 |

* cited by examiner

FLOW CONTROL VALVES FOR LEAKAGE DETECTION, FREE-FLOW PREVENTION AND OCCLUSION DETECTION

CROSS REFERENCE TO RELATED APPLICATION

This application is a continuation of PCT Application PCT/EP2009/060864, filed Aug. 24, 2009, which claims priority to European Patent Application No. EP 08163053.5, filed Aug. 27, 2008.

TECHNICAL FIELD

The present disclosure relates to a device for injecting a substance, in particular a fluid, into an organism, in particular a human and/or animal body.

BACKGROUND

The patient typically has to manually make one or more of the connections of a fluid guide system, an example of which is disclosed in U.S. Pat. No. 6,368,314 B1 which is hereby incorporated into by reference, with a risk that the connection is not properly made. In daily use it may be possible for one of these connections to be broken without the patient noticing. In addition, flexing of the fluid guide system can cause breakages in the tube, or the tube could be punctured, and in either case this could happen without being noticed by the patient. A leakage in the flow path that is not noticed by the patient or detected by the pumping system will result in an under-delivery of drug. Occlusion can occur when there is a blockage in the flow path. This may arise from for example by kinking of the tube. An occlusion results in an under-delivery of drug and then a subsequent bolus being given when the blockage is removed.

Free-flow prevention is important to ensure that over-delivery of the drug cannot occur. Free-flow can arise from a pressure difference between the atmosphere and the interior of the pump housing. This may occur due to a sudden drop in atmospheric pressure, for example from flying in a plane or going up a mountain in a cable car. A high pressure pushing on a piston (in the following called "displacement member") in the container that stores the drug will cause the piston to move forward and deliver drug into the patient which may be undesirable at that instant.

There are no methods for leakage detection in the flow path downstream of the adapter between the pump unit and the fluid guide system currently employed in infusion systems according to the present disclosure. The term of flow path within the framework of this application encompasses all parts of the injection device which function as a guidance of the fluid, for example adapters and valves, tubes of any kind, infusion sets and catheters which are used for guiding the fluid and any kind of fluid containers. Current methods for free-flow prevention include: Employing a sufficient friction of the displacement member in the container to prevent accidental movement of the displacement member, realizing a direct connection between the displacement member and a driven member which moves the displacement member, or inserting a valve into an adapter that links the container to the fluid guide system. In the following, the term "downstream" shall describe the direction of flow of the fluid to be administered which points towards the patient side end of the infusion system, i.e. towards the end of the catheter is inserted into the human and/or animal body. In contrast, the term "upstream" shall in the following denote the flow direction of the fluid to be administered which points in the direction the container.

Current methods for occlusion detection involve measuring the pressure in the flow path through the resultant force acting on the driven member that pushes against the displacement member. A force sensor is mounted behind the driven member and detects this force. For details about such a force sensor, it is referred to U.S. Pat. No. 6,368,314 B1. Alternative methods involve measuring the current through the drive motor.

It is desirable to have a means of pressure testing and free-flow prevention which allows for testing the pressure in and prevents free-flow from as many parts of the device. It therefore is preferable to have a control valve that is operable for pressure testing and is situated as far downstream as possible, in the best case just before the catheter tip that is inserted into the human and/or animal body. A control unit may further enable operation of the control valve and run a method for pressure testing before each administration of fluid in order to prevent administering a wrong dose to the organism.

SUMMARY

Included are embodiments of an injection device for injecting a fluid into an organism. In one embodiment, the injection device can comprise a fluid providing section which includes a container for storing the fluid and a supply means for supplying the fluid, a fluid injecting section for injecting the fluid provided by the fluid providing section into the organism and includes a catheter means. The fluid injecting section may be provided with a pressure recognition arrangement located at least close to the catheter means for detecting a pressure increase or a pressure loss.

DETAILED DESCRIPTION

According to the present disclosure, the injection device comprises a fluid providing section including a container for storing the fluid and a supply means for supplying the fluid. The device further includes a fluid injecting section which is provided with a pressure recognition arrangement which is located close to and/or in the catheter means for detecting a pressure increase or a pressure loss. This pressure recognition arrangement may include one or more valves which may be placed in the fluid injecting section, i.e. in the flow path downstream from the connection between the adapter and the container. The term of fluid providing section herein forth encompasses but is not limited to the container for storing the fluid and the supply means for supplying the fluid. The term of fluid injecting section herein forth encompasses but is not limited to an adapter which leads from the container to a fluid guide system, a fluid guide system, an infusion set and a catheter means as well as the connection parts between these components; the term of fluid injecting section may therefore be used in exchange for the term of flow path. In other words, the fluid injecting section comprises the walls of the flow path which are formed by the parts of the injection device which are in contact with the fluid. The term of pressure recognition arrangement herein forth encompasses but is not limited to at least one valve (control valve), an fluid pressure sensor, a control unit and a permanent memory.

A valve can be placed within each section of line that has a connector that can be connected and disconnected. The valve maintains a pressure in the line until the connection is broken or there is a leak, in which case the pressure in the flow path will drop. This loss or drop in pressure will be detected by an fluid pressure sensor and an alarm can be output by an alarm device. If the connection is not properly made in the first place, then the line pressure is not achieved during priming of the container and this will also be detected and an alarm output.

It is in particular envisaged that one control valve is placed in the infusion set, i.e. in the flow path of the fluid between the connection of the fluid guide system to the infusion set and the connection of the infusion set to the catheter. A further valve could also be placed in the fluid guide system, i.e. in the flow path between the connection of the adapter to the fluid guide system and the connection of the fluid guide system to the infusion set. Previously this has been considered impracticable, due to the need of keeping the infusion set as small as possible. However, flow restriction can be achieved through miniature valves, such as those manufactured by the Lee Company or by Bartels.

The time required to detect an occlusion depends upon the compliance in the system and the flow rate of the drug. The term of compliance C hereby means a change in volume $\Delta V$ in the flow path divided by a change in pressure $\Delta P$ in the flow path according to the equation $$C = \frac{\Delta V}{\Delta P}.$$

Such a change of volume may in the case of an occlusion be caused by the additional pressure exerting a force onto the walls of the flow path and thereby dilatating them and increasing the volume of the flow path. In the case of a leakage, the force exerted onto the walls of the flow path is lower than in the case of nominal pressure, and the walls may shrink and thereby decrease the volume of the flow path. The pump must attempt to administer enough drug volume in order for the pressure to build in the system to a sufficient level to detect a blockage. In highly compliant systems with low drug delivery rates a time of several hours may be required before an occlusion is detected. By placing a valve as close to the point of delivery as possible, such as in the infusion set just before the connection between the infusion set and the catheter that penetrates the skin, the system shall be maintained at the pressure that lies below an occlusion pressure, while removing a degree of compliance from the system. The degree of compliance is removed because the fluid pressure sensor may then detect a signal indicative of an occlusion and/or leakage which is valid for a larger portion of the fluid guide system than if the sensor were placed further upstream. Thus the time to detect an occlusion and/or a leakage can be substantially reduced.

Thus, a problem to be solved by the present disclosure can be defined as to reduce the time necessary for detecting an occlusion and/or a leakage in a device for administering a substance, in particular a fluid, into an organism, in particular a human and/or animal body.

The injection device according to one embodiment of the present disclosure for injecting a fluid into an organism, in particular a human or animal body, comprises a fluid providing section including a container for storing the fluid and a supply means for supplying the fluid, a fluid injecting section for injecting the fluid provided by the fluid providing section into the organism including a catheter means. The injection device is further provided with a pressure recognition arrangement which is located close to and/or in the catheter means for detecting a pressure increase and/or a pressure loss.

The injection device can furthermore comprise at least one control valve which is located in the fluid injecting section and is suitable for maintaining a pressure in the flow path. The valve can be a cracking valve, i.e. a pressure relief valve that opens and closes at a given cracking pressure. The term cracking pressure hereby encompasses a certain pressure which has to be attained or exceeded in order for the valve to permit flow through the valve. Examples of such valves include silicone membranes, micro-machined membranes or spring loaded balls that press against a seat. If the pressure lies below the cracking pressure, no flow through the valve should occur.

According to another embodiment of the present disclosure, the control valve can be operated, i.e. actively opened and/or closed and/or partially opened and/or partially closed by a controller. For example, a piezo-bending element that is electrically driven could open a membrane to allow flow. The movement of the flow regulating mechanism of the control valve can be initiated by signal emitted from a control unit (controller) of the injection device. This approach has the advantage that the system can be pressure tested, and the fluid pressure sensor (i.e. a sensor for measuring the pressure in the flow path) is activated for detection every time the drug is injected. For example, the drive unit can be activated to increase the pressure (e.g. over a predetermined value) in the flow path by driving the displacement member in the necessary (e.g. downstream) direction, then driving it in a (e.g. upstream) direction in order to decrease the pressure (e.g. below a predetermined value) in the flow path (in order to avoid later administration of a large bolus of fluid when opening the control valve again), whilst the control valve remains closed. After the pressure has been increased and before the drive unit is driven to decrease the pressure again, the fluid pressure sensor may be activated for detection of the pressure in the flow path. A control unit (i.e. a processor) can then compare the detected pressure value to a predetermined pressure value which should be achieved by the movement of the displacement member (e.g. in accordance with the fluid filling level of the injection device, i.e. how much fluid is available in the flow path). This predetermined value may be saved in a permanent memory belonging to the device and read for comparison by the processor. If there is no difference between the predetermined and the measured value (or a difference between the values lies within a certain predetermined interval) the valve can be opened to administer the drug. If there is a difference between the values (i.e. a difference of the values lie outside certain a certain predetermined interval), it is preferable to keep the value closed in order to avoid false administration of the drug. In this case, the controller may send a signal to an alarm device of the injection device which outputs corresponding information, e.g. a visual, audio and/or vibrational warning. If there is no difference between the measured value and the reference value (i.e. if the difference of the values lies within a certain predetermined interval), the controller may send a signal to the alarm device which outputs corresponding information, e.g. a visual, audio and/or vibrational message that the device works as planned. The control valve may then be opened again by a signal emitted from the controller and the drive unit may be driven in order to administer the fluid. Within the framework of this application, the term administration encompasses both completely continuous infusions and individual injections of a substance into an organism. The terms infusion and injection shall furthermore be used as synonyms.

The valve maintains a pressure in the flow path that can be detected by a force sensor used to detect an occlusion (i.e. the fluid pressure sensor). The standard line pressure (i.e. the reference or nominal pressure value) in the flow path would be below the pressure used to detect an occlusion and above the pressure used to detect a leakage. If the connection is broken, or there is a leakage, then the reference pressure in the system will not be maintained and this will be detected by the fluid pressure sensor. An occlusion shall therefore be assumed if the measured pressure value lies a predetermined amount above the reference pressure value. A leakage shall be assumed if the measured pressure value lies at a predetermined amount below the reference pressure value.

When the patient first connects the infusion set to the pump, the system will be pressurized. If the patient has not properly made the necessary connections, then the system will be unable to achieve the required line pressure and an alarm signal will be output by an alarm device.

If more than one valve is used in the system, then the valves can be configured to have different cracking pressures at which flow will occur. The valves may be arranged so that the cracking pressures of the valves increase with increasing distance downstream from the pump unit. This architecture will enable the location or the leak to be detected within the system downstream from the displacement member. In addition to detecting leakage, a valve with a high enough cracking pressure will also prevent free-flow. Free-flow is the flow which occurs due to the fluid's own gravitational force without further action by the injecting device. Such free-flow will then also be prevented for the fluid comprised in the flow path upstream of the control valve.

The container may be shaped in the form of an a cartridge as it is usually employed in the field of medical technology. The supply means can comprise a driven member and a displacement member. The driven member may be constructed as a threaded rod and pushes on a surface of a piston which constitutes at least part of the displacement member. The supply means may further comprise a driving unit (e.g. an electric motor or a spring-loaded driving mechanism) for driving the driven member. The driving unit, the driven member and the displacement member may form at least part of a pump unit. By pushing the fluid out of the container it is supplied to the flow path. A catheter is further used to connect a device to the organism, for example by penetrating the skin and/or further tissue, thereby enabling in particular intramuscular, intravenous, subcutane and/or intra-arterial infusions. The catheter may be connected to or form part of an infusion set which is part of the flow path.

The at least one control valve may advantageously in one embodiment be placed in the fluid injecting section, advantageously in another embodiment the infusion set, a further control valve or a multitude of further control valves, and in still other embodiments can also be placed in other parts of the flow path. The sensor for sensing an occlusion and/or a leakage (within this application designated as "fluid pressure fluid pressure sensor") is a sensor which detects the pressure of the fluid in the flow path. The device compares this detected, i.e. measured value with at least one reference value which may be saved in a permanent memory of the device. The measured value may also be saved for further use. This comparison can for example be performed by a processor which is configured to perform the comparison. A result of this comparison can be output by the processor and can serve as a basis for an information which is supplied. The comparison of the measured value with the at least one reference value may lead to a result which indicates that the measured value is equal to the reference value or higher or lower than the reference value. Furthermore, an allowable interval reaching above and/or below the reference value may be given, and if the measured value lies within this interval, the result of the comparison may comprise information that the measured value lies in the allowable interval. The reference value itself may also form an upper and/or lower boundary of the allowable interval. Independently of whether the reference value lies on a boundary of the allowable interval or not, the allowable interval is in the framework of this application said to be located "around" the reference value. The measured value may be used to extrapolate a pressure deviation from the reference value in order to detect a tendency of the measured value approaching a boundary of the allowable interval. Corresponding information may be output by the device, for example a warning about a tendency of the measured value to reach a value which is indicative of a leakage or occlusion of the flow path. This may be done by saving at least one measured pressure value in the permanent memory and comparing it to a reference value or by comparing a measured and subsequently saved value with another measured and subsequently saved value. The information supplied based on the results may be imagined as an audio and/or visual information and/or a vibrational signal which is transmitted by the device, the recipient of the information being for example a human and/or an animal being (e.g. medical personnel, a human and/or animal patient, or any other person) and/or a technical device (e.g. a control unit controlling a control valve and/or a drive unit of the supply means, the supply means comprising the driven member and the displacement member). The result of the comparison may be output by the controller, and the processor can be configured to supply the information based on the result via an acoustic device (e.g. a conventional loudspeaker), a display means (based e.g. on cathode ray tube technology or liquid crystal display technology, or comprising a light emitting diode and/or a light bulb) and/or a vibrational device (e.g. a vibrational motor).

In case of more than one control valves being installed in the flow path, at least one of the control valves may have a cracking pressure which is different from the cracking pressure of at least one other control valve. In other words, if the device comprises more than one, i.e. at least two of the above-mentioned control valves, they can be arranged in such a manner that they have cracking pressures which are different between at least two of the valves. This arrangement can furthermore be designed such that the cracking pressures of the valves increase with increasing distance along the flow path downstream from the displacement member. In this sense, at least one of the valves has a cracking pressure which is higher than a cracking pressure of another valve which is located along the flow path closer to the displacement member.

By placing a control valve in the infusion set directly upstream of the connection between the infusion set and the catheter, a pressure test of the whole flow path up to that location of the control valve becomes possible. Additionally, free-flow is prevented for the fluid contained in the flow path in any part of the flow path upstream of the location of the control valve. Free-flow of the fluid is prevented as long as the pressure exerted by the gravitational force of the fluid onto the control valve is less or less or equal to the cracking pressure of the control valve. For example, whenever the fluid shall be administered the control valve can be closed before actual administration of the drug. The supplying means will then be driven by the driving unit to exert a pressure on the flow path. The driving may to this end receive a signal from the processor. This closing of the control valve may be performed by a control unit which e.g. receives a signal from the drive unit or which e.g. runs a program controlling the actions of the whole injection device. The signal may contain information which tells the control unit to drive a mechanism of the control valve in order to prohibit flow through the control valve. In the case of a program run by the control unit, this program may contain an instance at which a signal is sent to a mechanism of the control valve in order to close it such that flow through the valve is prohibited. Such a closing may be irrespective of the cracking pressure of the control valve, i.e. the control valve may remain closed even if the applied pressure is higher than its cracking pressure. Preferably, the applied pressure is at least as high or higher than the highest cracking pressure of any of the control valves, whereby a pressure test over all pressure values which are applied during routine administration becomes possible. The fluid pressure sensor can then measure the pressure in the flow path and a control unit can then decide by comparing it with a known pressure value to be achieved by the action of the supply means whether there is an occlusion or a leakage in the flow path. To this end, the fluid pressure sensor is activated to measure the pressure. Placing the control valve immediately upstream of the upstream end of the catheter makes it possible to draw a conclusion for the presence of a leakage or occlusion for all parts of the flow path downstream to that position. Placement of the specific control valve at a location further upstream would not allow for detection of leakage or occlusion downstream of the position of the control valve. One of the main purposes of the fluid pressure sensor is to measure an occlusion or a pressure drop.

The device for injecting a fluid into an organism may further comprise a permanent memory (such as e.g. a magnetic memory device, an EEPROM, a CD-ROM and/or a DVD) which is configured to store at least one nominal value for the pressure of the fluid. This nominal value may be predetermined and can comprise an allowable interval stretching above and/or below the reference value, i.e. nominal value. Also at least one of the pressure values measured by the fluid pressure sensor may be stored in the permanent memory for later use as a reference value. The device then further comprises a controller or control unit (which may comprise a processor) which is configured to compare the at least one reference value for the pressure of the fluid with at least one of the measured values for the pressure fluid. To this end, the processor can be configured to read at least one reference value and/or at least one measured value from the permanent memory. The processor may also be configured to write such values to the permanent memory. The processor may be incorporated into a computer (e.g. a personal computer, a laptop, or a microcomputer) such that the computer runs a program comprising the steps of the above-described method, wherein this program may be stored on a permanent or temporary memory medium, a data carrier or the like.

Figure 1:
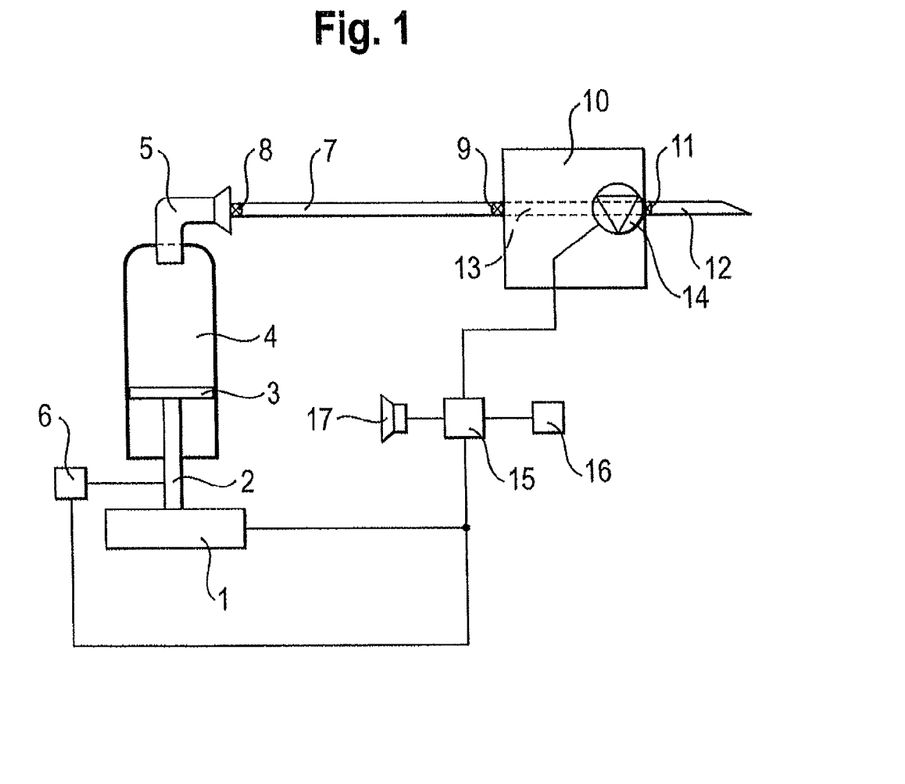
FIG. 1 shows an embodiment of the disclosure with a control valve placed in the infusion set.

Referring now to the drawings wherein according to a first embodiment of the disclosure in FIG. 1, the injection device (1') may comprise an fluid pressure sensor 1 which can be coupled to a driven member 2 in order to measure the pressure which is exerted by the driven member 2 via the displacement member 3 onto the fluid which is contained in the container 4. The driven member 2 may be driven by a driving unit 6. The driving unit 6 can e.g. be an electrical motor or a driving mechanism which is governed by the force of a spring (a spring-loaded driving mechanism). The driven member 2 and the displacement member 3 may form parts of a supply means 2, 3. The supply means 2, 3 may further comprise the driving unit 6 which may then together with the driven member 2 and the displacement member 3 form part of a pump unit 2, 3, 6. The fluid providing section may include but not be limited to the container 4, the driven member 2, the displacement member 3 and the driving unit 6.

Connected to the volume of container 4 is an adapter 5 which permits transportation of the fluid from the container 4 into a fluid guide system 7. However, it is also usual to connect the container directly to the system 7. Such an adapter may have a form fit and/or a force fit into the container 4, and the connection 8 between the fluid guide system 7 and the adapter 5 may also be form fitting and/or force fitting. The connections of the adapter 5 to the container 4 and of the adapter 5 to the fluid guide system 7 (i.e. the connection 8) may also be constituted by an adhesive bond. The adapter 5, the connection 8, the fluid guide system 7, and the connection 9 between the fluid guide system 7 and an infusion set 10 as well as the connection between the infusion set 10 and a catheter means 12 may comprise material such as a rubber material or a plastic material of which fluid guiding parts of medical devices are usually made. Thereby, a certain flexibility and elasticity of the adapter 5, the connections 8, 9 and 11 and the fluid guide system 7 are allowed for. The fluid guide 7 may be connected to the infusion set 10 by a connection part 9; the connection of the connection part 9 to the infusion set 10 may be performed like the previously mentioned connections by a form fit, force fit and/or an adhesive bond. The infusion set 10 may be a catheter head as described in US 2007/0112303. Such an infusion set 10 comprises a flow line 13 for transportation of the fluid stretching from a part of the infusion set 10 which lies immediately downstream of a connection between the connection part 9 (i.e. a constituent of the flow path located upstream of the upstream end of the infusion set 10) and the infusion set 10 to a part of the infusion set 10 which lies immediately upstream of a connection between the connection part 11 and the infusion set 10 (i.e. a constituent of the flow path located downstream of the downstream end of the infusion set (10). The connection part 11 connects the infusion set 10 to the catheter means 12 and may also be connected to the infusion set 10 and/or the catheter means 12 with a force fit, form fit and/or an adhesive bond. The catheter means 12 will normally consist of a metal and/or plastic and/or rubber tube which is inserted into the tissue of a human and/or animal body for administration of the fluid to be injected. In the framework of this application the term of flow path encompasses but is not limited to parts of the device such as the displacement member 3, the container 4, the adapter 5, the connection parts 8, 9 and 11, the fluid guide system 7, the infusion set 10, the flow line 13, the control valve 14, and the catheter means 12. The term of flow path may also encompass only parts of this listing.

A control valve 14 may be placed in the infusion set 10 such that it may act on the flow line 13. The action of the control valve 14 on the flow line 13 includes but is not limited to opening and closing the flow diameter of the flow line 13.

Such opening and/or closing may comprise complete opening and/or closing and/or partial opening and/or closing of the flow line 13 such that flow of the fluid to be administered is enabled or not enabled, respectively. The control valve 14 will therefore be located at least partly within the volume (i.e. within the flow diameter) of the flow line 13 or in a part of the infusion set 10 in the immediate neighborhood of the flow line 13 such that the part of the control valve 14 which is meant to open and/or close the flow line 13 is able to do so. Preferably, the control valve 14 is located at or in the immediate vicinity of the end of the flow line 13 which connects to the connection part 11.

The action (i.e. operation) of the control valve 14 may be controlled by a controller or control unit or controller, e.g. a processor 15. The processor 15 can send signals to the control valve 14 upon which the control valve 14 performs a certain action that comprises in particular moving its valve mechanism in order to open and/or close the flow diameter of the flow line 13 or to open and/or close it at least partially. The processor 15 may read and/or write values to a permanent memory 16. Such values may include but are not limited to pressure values concerning the pressure of the fluid in the flow path. The processor 15 may also read values, i.e. in particular pressure values, from the fluid pressure sensor 1. The processor 15 is configured to compare a detected value with at least one reference value which may be stored in a permanent memory 16. The measured value may also be stored in the permanent memory 16 for further use. The permanent memory 16 may comprise a magnetic memory device such as usually employed in hard disks or flash memories, an optical memory device such as a CD-ROM or a DVD or a magnetic tape. In case the comparison performed by the processor 15 between the measured value and the reference value results in a difference between the two values which is undesirable, the processor 15 may give a signal to an alarm device 17 which is configured to emit a corresponding information, e.g. an audio signal, an optical signal and/or a vibrational signal. For this reason, the alarm device 17 may comprise but not be limited to an acoustic device (e.g. a conventional loudspeaker), a display means (based e.g. on ray tube technology or liquid crystal display technology, or comprising a light emitting diode and/or a light bulb) and/or a vibrational device (e.g. a vibrational motor). The processor 15 may also be connected to control the driving unit 6. For control of the driving unit 6, it may send a signal to the driving unit 6 which causes the driving unit 6 to drive the driven member 2 in a certain direction, i.e. either to drive the driven member 2 such that fluid is pushed out of the container 4 via the displacement member 3 or such that the driven member 2 is moved in the opposite direction. The processor 15 may also cause the driving unit 6 to stop moving the driven member 2. Form the above it becomes evident that a pressure recognition arrangement for the injecting device, in particular the fluid providing section and/or the fluid injecting section, may comprise but not be limited to at least on control valve 14, an fluid pressure sensor 1, the control unit or controller (processor) 15 and the permanent memory 16.

Figure 2:
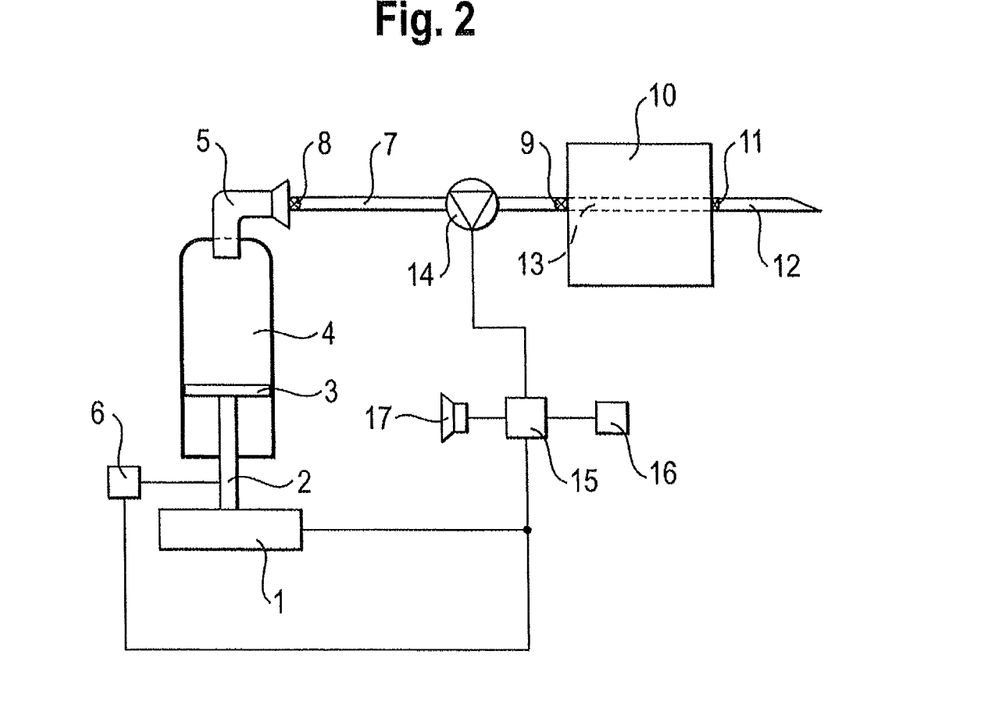
FIG. 2 shows an embodiment of the disclosure with a control valve placed in a part of the flow path outside the infusion set.

A second embodiment according to the disclosure is shown in FIG. 2. The configuration of the second embodiment is analogous to the first embodiment according to FIG. 1 with the exception of the location of the control valve 14. In this second embodiment according to FIG. 2, the control valve 14 is not placed within the infusion set 10, i.e. in particular not in the position as described in the first embodiment according to FIG. 1. In this second embodiment, the control valve 14 is placed along the flow path of the fluid to be administered in particular upstream of the end of the flow line 13 which connects to the connection part 9. In this case, the most downstream location of the control valve 14 which is possible, is at or in direct vicinity of the end of the connection part 9 which points to the flow line 13. Merely by way of example, FIG. 2 shows a control valve 14 located in the fluid guide system 7, i.e. the control valve 14 is located in a part of the flow path between the connection of the fluid guide 7 to the connection part 8 and a connection of the fluid guide 7 to the connection part 9. The control valve 14 may be located within or in the direct vicinity of the flow diameter of the fluid guide system 7 such that its action on the flow path is permitted. This action may, as in the first embodiment, comprise complete and/or at least partial closing and/or opening of the flow path of the fluid guide system 7 such that flow of the fluid to be administered is enabled or not enabled, respectively.

Figure 2A:
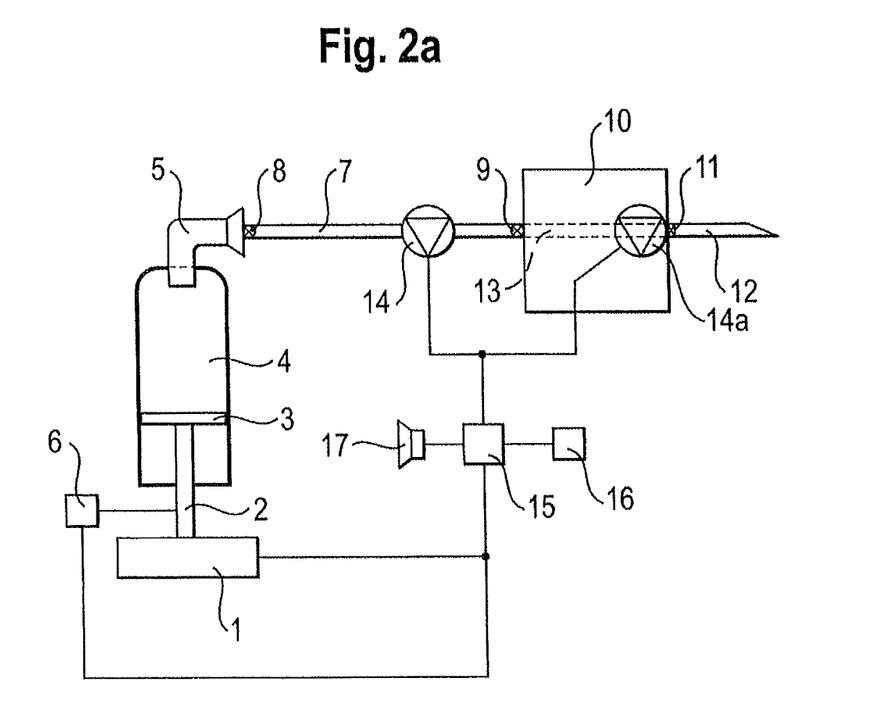
FIG. 2a shows an embodiment of the disclosure with a multitude of control values placed in the infusion set.

FIG. 2a shows a third embodiment of the disclosure which is essentially equal to the first and second embodiments with the exception of the employment of a multitude of control valves. This third embodiment shows a combination of the first and second embodiment, i.e. a control valve 14a according to the first embodiment is located in the infusion set 10 and a control valve 14 according to the second embodiment is located in the fluid guide system 7. The exact locations of the control valves 14 and 14a shall be described in analogy to the first and second embodiments. The employment of two control valves 14, 14a according to the third embodiment is shown in FIG. 2a by mere way of example, i.e. the two control valves 14, 14a may be complemented by at least one more control valve to form a multitude of control values, the locations of any of the control valves not being limited to the configuration shown in FIG. 2a. It is only important that the control valves are placed in such locations that they can exert the desired action on the fluid inside the flow path and/or the volume of the flow path itself. The desired action of the control valves comprises but is not limited to opening and closing the flow diameter of the flow path as described in the first and second embodiments. According to the third embodiment, the cracking pressures of the control valves may be different between at least two of the employed control valves, i.e. in the shown configuration of FIG. 2a between the control valve 14 and the control valve 14a. In order to avoid free flow for as many parts of the flow path of the injection device as possible, it is desirable that the cracking pressures of the control valves increase with increasing distance along the flow path downstream from the displacement member 3. Preferably, the control value which has the most downstream location has the highest cracking pressure. It may also be envisaged that all of the employed control valves have identical cracking pressures.

Figure 3:
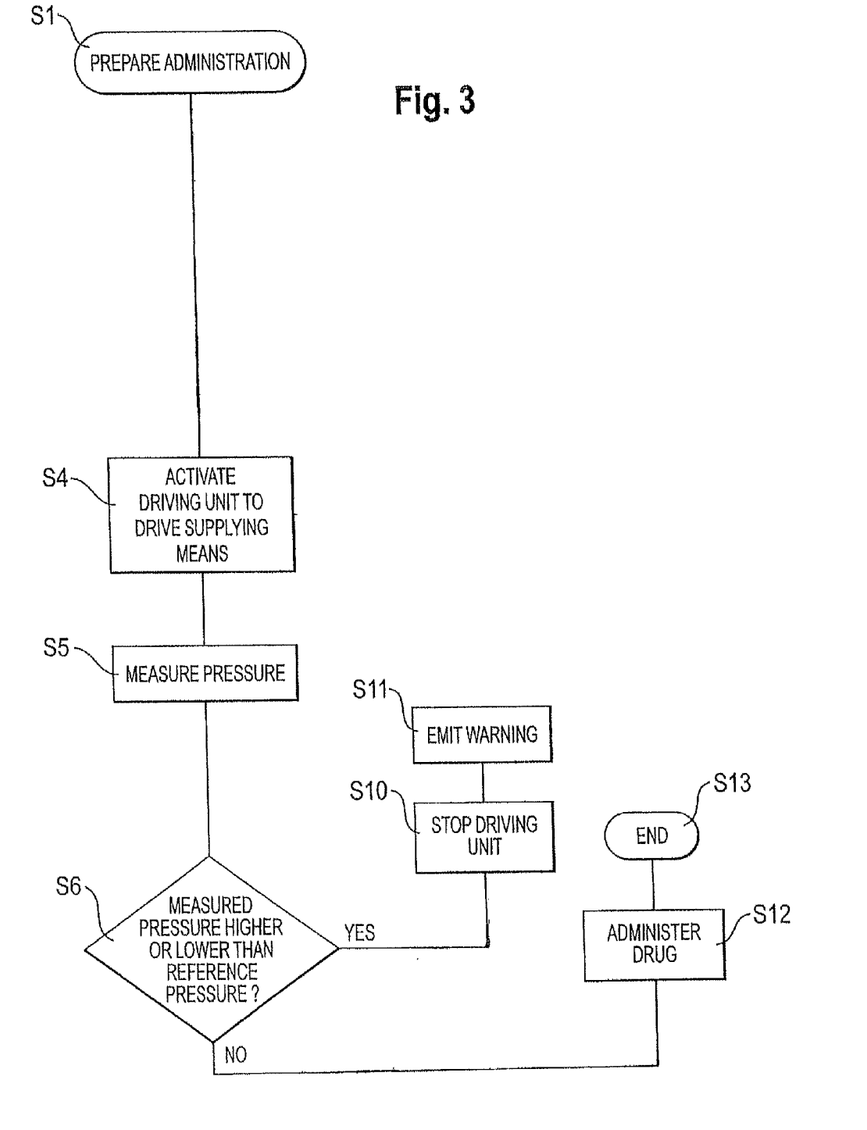
FIG. 3 shows a basic flow diagram of a method for pressure testing the flow path before administration of a drug according to the disclosure.
Figure 3A:
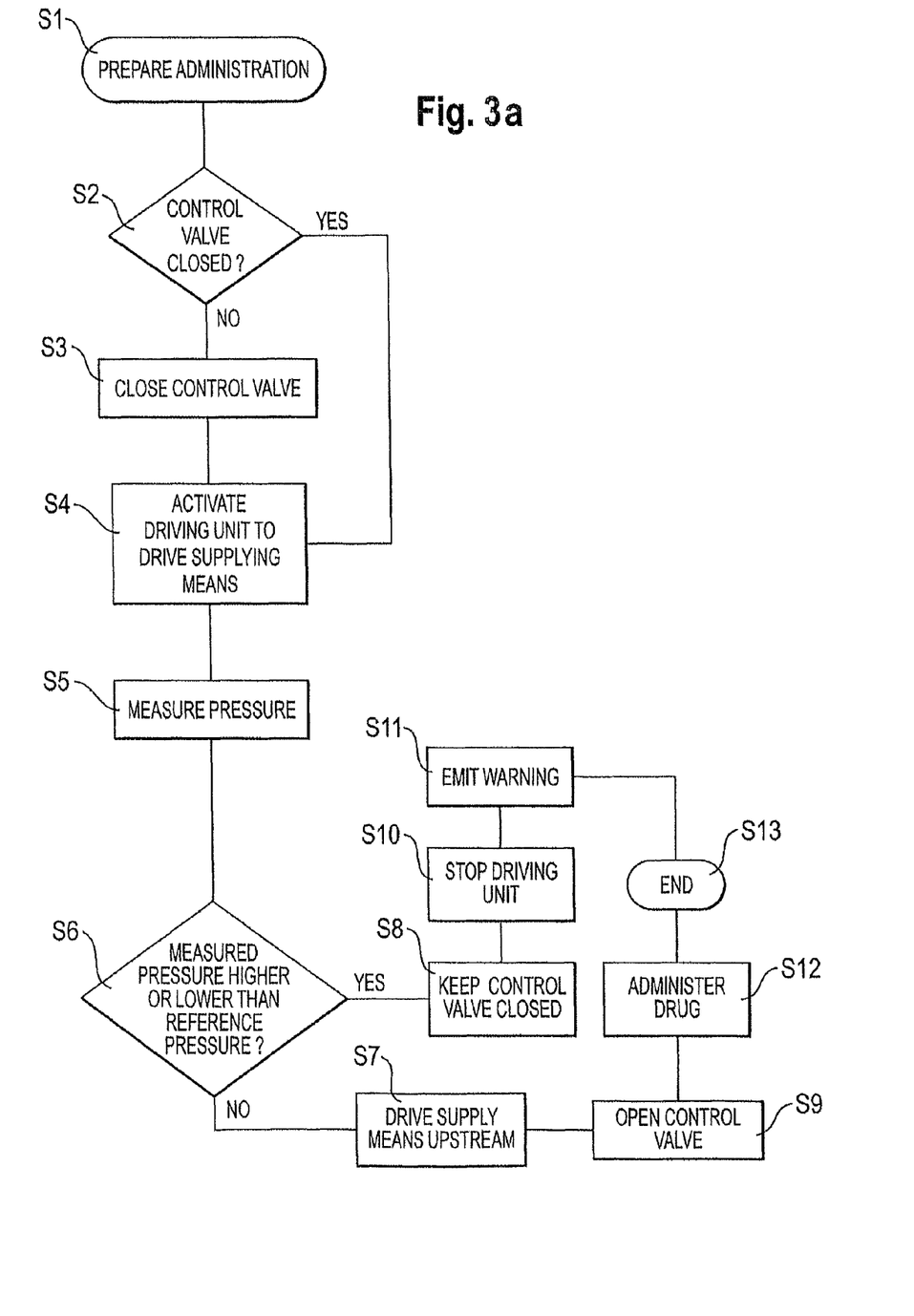
FIG. 3a shows another flow diagram of a method for pressure testing the flow path before administration of a drug according to the disclosure.

The present disclosure also relates to a method for pressure testing the device for injecting a fluid according to the diagram of FIG. 3a.

In step S1, the administration of the fluid is prepared. Such preparation may comprise the control unit or controller (i.e. the processor 15) reading an administration plan from the permanent memory 16. Such an administration plan may include but not be limited to the time of administration and/or the dose, i.e. volume of fluid to be administered.

In a step S2, the processor 15 sends a query signal to the control valve 14. The signal may also be sent to a predefined number of control valves 14, 14a if multiple control valves 14, 14a are employed in the injection device. This query signal asks for the state of each of the control valves, i.e. whether the control valve is opened or closed or e.g. at least partially opened and closed, i.e. in which position the flow regulating mechanism of the control valve is positioned at the time the query signal is sent to the control valve.

If the respective control valve is not completely closed, the processor 15 sends a signal to the respective control valve in step S3 in order to close the control valve. Preferably, such a closure is performed until the control valve is completely closed, i.e. until no fluid flow through the control valve is possible. If in step S2 the control valve is closed, the method carries on directly with step S4.

Step S4 comprises the processor 15 activating the driving unit 6 in order to drive the supplying means, i.e. in particular the driven member 2. The driven member 2 shall be driven in such a direction that pressure is exerted on the fluid in the flow path of the device such that the fluid is pumped downstream from the displacement member 3 or the pressure in at least the part of the flow path upstream of the location of the closed valve is increased due to at least one control valve being closed. This means that the displacement member 3—being attached to the driven member 2—is preferably driven in a downstream direction. The driving of the driven member 2 may be performed until a predetermined test pressure is achieved in the flow path up to the control valve.

Also with reference to FIG. 3a, after administration has been prepared in accordance with step S1, it is preferred to check whether the control valve is open or closed (step S2) and to close this valve to cause a basic condition (step S3).

The control valve which is closed in step S3 may preferably be placed at the location of the control valve 14 in the first embodiment according to FIG. 1. Thereby, a pressure test of the whole flow path between the displacement member 3 and the position of the control valve 14 becomes possible. The predetermined pressure up to the achievement of which the driven member 2 is driven may be read by the processor 15 from the permanent memory 16. The measurement of the pressure may be performed by the fluid pressure sensor 1 during the whole procedure described by the diagram of FIG. 3a, i.e. by the method for pressure testing according to the present disclosure. The processor 15 will receive a signal from the fluid pressure sensor 1 containing information about the pressure value measured by the fluid pressure sensor 1. The control unit 15 can then perform a comparison between the measured pressure value and e.g. a predetermined pressure value which may be saved in and read from the permanent memory 16. A measured pressure value may also be stored by the processor 15 in the permanent memory 16 for later use, i.e. in particular for comparison with another measured pressure value.

In step S5 of the method, the fluid pressure sensor 1 measures the pressure in the flow path of the device and sends the measured pressure value to the processor 15. The processor 15 may compute whether a certain (i.e. reference) pressure value has been reached. This may be determined by equality of the measured pressure value to a predetermined reference pressure value or by the measured pressure value lying in a predetermined allowable interval around, i.e. above and/or below a reference value. The reference value may within the formulation "around" also lie on a boundary of the allowable interval. Information pertaining to such an allowable interval may also be saved in the permanent memory 16 and read by the processor 15 for use in the comparison with the measured pressure value.

The comparison of the measured pressure value to a reference pressure value is performed in step S6. If the reference pressure value is not achieved by the driven member 2 even though it has been driven to such a position that this reference pressure value should have been achieved, the processor 15 may keep the control valve 14 closed, stop the driving unit 6, and emit a warning signal to the alarm device 17 which will then output an information as described above. The position of the driven member 2 corresponding to the reference pressure value may be determined by the driving unit 6 and communicated to the processor 15 which may compare the measured position of the driven member 2 to a reference position connected to a reference pressure value which may be stored in and read from the permanent memory 16.

Step S6 relates to a comparison of the pressure value measured by the fluid pressure sensor 1 to a reference pressure value which may be stored in and read from the permanent memory 16, all these actions being performed by the processor 15. The comparison of the measured value to the at least one reference value may lead to a result which indicates that the measured value is higher or lower than the reference value. It may also indicate that the reference value and the measured value are equal. An allowable interval reaching above and/or below the reference value may also be given, and if the measured value lies within this interval (which situation may be determined by the comparison performed by the processor 15), the result of the comparison may comprise information that the measured value lies in the allowable interval. The measured value may then be used to extrapolate a pressure deviation from the reference value in order to detect a tendency of the measured value approaching a boundary of the allowable interval. Corresponding information may then be sent by the processor 15 to the alarm device 17 which may output a respective signal (i.e. information). Such determination of a tendency of a measured value may be done by saving at least one measured pressure value in the permanent memory 16 and comparing it to a reference value or by comparing a measured and subsequently saved value with another measured and subsequently saved value. The at least two measured and subsequently saved values which are compared may be two consequent values in the sense that they were measured in two adjacent time steps. There may also be a multitude of time steps and/or measured values which lie in between the time steps and/or measured values which are compared. The tendency determination may include a combination of the measured values to compute a trend curve which may then be evaluated with respect to the reference pressure value and/or the allowable interval around the reference pressure value.

If the measured pressure is not equal to the reference value or does not lie not within the allowable interval given around the reference value, the processor 15 will in step S8 keep the control valve closed. In step S10 the driving unit 6 will then be stopped by the processor 15 in order not to drive the driven member 2 and a warning signal is sent by the processor 15 to the alarm device 17 which may output corresponding information in step S11.

Should in step S6 it be determined that the measured pressure value is equal to the reference pressure value or that it lies within the allowable interval predetermined around the reference value, the processor 15 will give a signal to the driving unit 6 in order to drive the driven member 2 into a direction opposite to the direction resulting from step S4, i.e. in particular in a direction such that the pressure of the fluid in the flow path is reduced. This means, that the displacement member 3—being attached to the driven member 2—is preferably driven in an upstream direction. It is in addition to the diagram of FIG. 3a envisaged that the processor 15 then sends a signal to the alarm device 17 which includes information about the measured pressure value being equal to the reference pressure value or lying within the allowable interval around the reference pressure value. The alarm device 17 may emit information based on this signal.

The processor 15 may then in step S9 send a signal to the control valve in order to open it or to open it at least partially, so that flow through the flow valve is no longer prohibited. In step S2 the processor 15 then drives the driving unit 6 to move the driven member to such that fluid is administered to the human and/or animal body according to the administration plan mentioned in step S1. In this case, the displacement member 3—being attached to the driven member 2—is preferably driven in upstream direction.

If more than one valve is arranged in the flow path, it is possible to detect the location of an occlusion or a leak by actuating the valves in different sequences and by monitoring whether the pressure drop or the excessive pressure increase still occurs. If every valve is provided with a fluid pressure sensor, it is possible to get the maximum information about the calculation of an occlusion.

The embodiments of this present disclosure describe a device for administering fluid into an organism, in particular a human and/or animal body which comprises at least one control valve located such that as many parts of the flow path of the fluid are safeguarded from free-flow. Furthermore, the device includes a control unit for driving a regulating mechanism of a control valve and a driving unit for driving a pump unit and an fluid pressure sensor which may operate together to perform a pressure test of as many parts of the flow path as possible before each administration of the fluid, the control valve being placed at a suitable location for such a test.

A simplified variation of the method according to the present disclosure is illustrated with reference to FIG. 3. There, an administration operation is prepared according to step S1. Then, in step S4, the driving unit is activated to increase the pressure and this pressure is measured (step S5). If the pressure exceeds a predetermined pressure threshold or equals thereto, the driving unit can be stopped (step S10), while in case the measured pressure is lower than the threshold the enabled drug can be administered (step S12). Afterwards, the administration process can be terminated at step S13, e.g. with a certain end of administration signal. On the other hand, if the driving unit was stopped at step S10, a warning could be communicated (step S11).

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modifications and variations come within the scope of the appended claims and their equivalents.

What is claimed is:

1. An injection device for injecting a fluid into an organism, the injection device comprising:
   a fluid providing section including a container for storing the fluid and a pump unit for supplying the fluid, the pump unit comprising a displacement member, a driven member and a driving unit; and
   a fluid injecting section for injecting the fluid provided by the fluid providing section into the organism and a catheter means, wherein
   the fluid injecting section is provided with a pressure recognition arrangement for detecting at least one of a pressure increase and a pressure loss in the fluid injecting section, the pressure recognition arrangement comprising a fluid pressure sensor, a control unit, a permanent memory, and at least one control valve, the at least one control valve is a cracking valve that opens the at least one control valve above a cracking pressure, permitting flow through the at least one control valve, and closes the at least one control valve below the cracking pressure, wherein the control unit is configured to extrapolate a time series of measured pressure values in the fluid injecting section and to send a signal to an alarm device if the extrapolated values attain a certain relation to at least one given reference pressure value.

2. The injection device according to claim 1, wherein the control unit is configured to operate the pressure recognition arrangement.

3. The injection device according to claim 1, further comprising a plurality of control valves, the plurality of control valves are cracking valves that open and permit flow through the plurality of control valves above the cracking pressure, and closes the plurality of control valves below the cracking pressure, wherein the plurality of control valves are configured to have different cracking pressures at which flow through the plurality of control valves will occur.

4. The injection device according to claim 1, wherein the permanent memory is configured to store at least one reference value for the pressure of the fluid.

5. The injection device according to claim 1, wherein the fluid pressure sensor senses at least one of pressure, occlusion and leakage in the fluid injecting section and sends a measured value to the control unit, wherein the control unit compares the measured value to at least one reference value and outputs a result of the comparison of the measured value and the at least one reference value, based on the result an information signal is supplied.

6. The injection device according to claim 5, wherein the information signal is sent to an alarm device, wherein the information signal can give rise to a corresponding information emitted by the alarm device.

7. A method of controlling an injection device according to claim 1 comprising:
   providing the control unit to operate the pressure recognition arrangement of the injection device, said control unit measures the pressure in the fluid injecting section and compares the measured pressure value to at least one reference pressure value and a predetermined interval around the reference pressure value, and if the measured pressure value is not equal to the at least one reference pressure value or does not lie within a predetermined interval around the reference pressure value, the control unit stops the driving unit which is operably connected to the fluid providing section of the injection device.

8. The method of claim 7, further comprising issuing an alarm from the control unit to an alarm device.

9. The method of claim 7, further comprising:
   checking whether the pressure recognition arrangement is in a state to detect the pressure increase or the pressure loss; and
   if the pressure recognition arrangement is not in a state to detect the pressure increase or the pressure loss, enable the pressure recognition arrangement to detect the pressure increase or the pressure loss.

10. The method of claim 7, further comprising:
    stopping the driving unit if the position of the driven member of the injection device is not in accordance with a predetermined position of the driven member relative to the measured pressure value;
    driving the driven member such that the pressure in the fluid injecting section is reduced; and
    emitting a signal based on the comparison of the measured pressure value to at least one of the reference pressure value and a predetermined interval around the reference pressure value.

11. The injection device according to claim 3, wherein the plurality control valves are arranged such that the cracking pressures of the plurality of control valves increase with increasing distance from the pump unit downstream along the fluid injecting section.

* * * * *